United States Patent [19]

Holt et al.

[11] 4,058,762
[45] Nov. 15, 1977

[54] METHOD AND APPARATUS FOR MAGNETIC INSPECTION THROUGH ADJUSTABLE PULSED ALTERNATING AND DIRECT CURRENT MAGNETIC FIELDS

[75] Inventors: Amos Earl Holt; William Eugene Lawrie, both of Lynchburg, Va.; Albert Stingel Birks, Doylestown, Ohio

[73] Assignee: The Babcock & Wilcox Company, New York, N.Y.

[21] Appl. No.: 693,021

[22] Filed: June 4, 1976

[51] Int. Cl.² .............................................. G01R 33/12
[52] U.S. Cl. ...................................................... 324/216
[58] Field of Search ..................................... 324/37, 38

[56] References Cited

U.S. PATENT DOCUMENTS

| | | | |
|---|---|---|---|
| 1,782,462 | 11/1930 | Chappuzean et al. | 324/37 |
| 1,910,770 | 5/1933 | Kinsley | 324/37 |
| 3,378,762 | 4/1968 | Parker | 324/38 |

FOREIGN PATENT DOCUMENTS

| 447,838 | 4/1948 | Canada | 324/38 |
|---|---|---|---|

Primary Examiner—Robert J. Corcoran
Attorney, Agent, or Firm—J. Maguire; R. J. Edwards

[57] ABSTRACT

An illustrative embodiment of the invention provides a method and apparatus for magnetic inspection of areas of interest in ferromagnetic material by means of both alternating and direct current induced magnetic fields. Moreover, the magnetic fields may be pulsed sequentially and/or simultaneously to detect defects deep within the area of interest.

5 Claims, 5 Drawing Figures

METHOD AND APPARATUS FOR MAGNETIC INSPECTION THROUGH ADJUSTABLE PULSED ALTERNATING AND DIRECT CURRENT MAGNETIC FIELDS

BACKGROUND OF THE INVENTION

1. Field of the Invention

This invention relates generally to nondestructive testing, and more particularly, to nondestructive magnetic particle inspection of ferromagnetic material and the apparatus therefor.

2. Description of the Prior Art

The use of electric current to create or induce a magnetic field in ferromagnetic material to test the material for flaws, defects or discontinuities, hereinafter called "defects", in areas of interest, such as weldments, is well known. Moreoever, the magnetic inspection method is well known for detecting both surface and subsurface defects which create detectable perturbations or distortions in the induced magnetic field. In general, the defects distort the induced magnetic field in the ferromagnetic test material producing a leakage field external to the test material and also creating opposing magnetic polarities across the defects which, among other things, will attract an accumulation of magnetic particles applied to the surface of the material if the magnetic field perturbation is of sufficient strength to penetrate the surface of the material.

Accordingly, magnetic particle inspection, as it is commonly known in the art, comprises three basic operations: creating or inducing a suitable magnetic field in the test material; applying a powder or suspension of magnetic particles on the surface of the test material in the area of the induced magnetic field and inspecting the material's surface for accumulations of particles, that is, indications of defects, e.g. cracks, holes, slag entrapment, lack of penetration of fusion due to an improper weld, and the like.

Although the magnetic field of the magnetic particle inspection method may be induced in the test material by a permanent magnet, the most commonly created magnetic fields for this type of nondestructive testing are induced by electric current flow, such as, direct, alternating and half wave rectified current. Direct current, for instance, induces a time invariant magnetic field in response to the constant direct current which penetrates deep within the material and, accordingly, affords subsurface defect detection. Alternating current, however, induces an alternating magnetic field, in response to the current, which is limited by skin effect to the surface of the material and, therefore, to surface defect detection only. Half wave rectified current, that is rectified alternating current, in effect is a combination of direct current and various harmonics of the alternating currents and affords surface and subsurface defect detection.

However, each of these magnetic inspection techniques are limited to a certain extent. For example, a direct current supply such as a storage battery is limited in the magnitude and duration of available current. Furthermore, the constant direct current induces a constant magnetic field which attracts the magnetic particles and holds them fixed in position along magnetic lines of force. And, in addition, the direct current test may cause material burn due to excessive continuous current. Alternating current, moreover, is limited to surface detection only, because the magnetic field strength associated therewith decreases exponentially into the material. However, alternating current provides a dynamic motion to the particles in response to the induced varying magnetic field. Half wave rectified current likewise produces a motion in the particle powder but the subsurface component of the induced magnetic field is limited to some extent by the rectified alternating current fields at the surface of the material, which may interfere with the subsurface defect detection.

Accordingly, for magnetic particle inspections of test materials in which half wave rectified current does not produce satisfactory results two tests are required, a subsurface or direct current test and a near surface alternating current test. Clearly, from an economic point of view a substantial savings can result from a single test system or one which readily performs both deep subsurface and surface detection. In addition, the prior art methods generally require the skill of a trained inspector to determine the nature, location and extent of the indications by examination of the influenced magnetic particle powder.

Therefore, there is a need to provide industry with an apparatus for nondestructive magnetic inspection of areas of interest of test materials which economically and efficiently inspects the material for both subsurface and surface defects, enhances the detection of deep subsurface defects and which improves the response of the particles to the magnetic field for ease of observation of any defects.

SUMMARY OF THE INVENTION

According to the invention a method of and means for magnetically inspecting an area of interest, such as a weld seam, in ferromagnetic materials are provided. Illustratively, the apparatus of this invention includes an alternating current circuit and a direct current circuit arranged in parallel with each other and in series with the material to be tested. Moreover, the process characterizing the invention is, essentially, a form of alternating current and direct current magnetic particle inspection of subsurface and surface defects, which also enhances deep subsurface defect detection and improves the observed response of magnetic particles to the disturbed magnetic fields.

Specifically, the magnetic inspection apparatus of the invention includes an alternating current circuit, having a filter therein to prevent the passage of direct current therethrough, which induces an alternating magnetic field, in response to the current, in the test material connected thereto. In addition, a direct current circuit, having a filter or "choke" therein to prevent alternating current flow therethrough, is connected in parallel with the alternating current circuit and likewise is also connected in series with the material to be tested. Accordingly, the direct current circuit of this invention induces a deep penetrating magnetic field in the test material and the alternating current induces an alternating near-surface magnetic field. Independent control of the direct and alternating currents increases the detection of the direct current induced leakage fields created by deep subsurface defects and, also, provides an improved observable response of the magnetic particles to the leakage fields.

More specifically, a magnetic particle inspection device according to this invention comprises an alternating current circuit, including in series a direct current filter and a standard adjustable electrical time delay relay, for rate and duration regulation of the alternating current. Furthermore, a direct current circuit is connected in parallel with the alternating current circuit and includes in series an alternating current filter or "choke" and a standard adjustable electrical time delay relay, as above. Both circuits are connected in series with a yoke, wherein the electrical current, alternating and direct or either, through the yoke induces a magnetic field, responsive to the current, in a test material connected scross the end portions of the yoke. Furthermore, a single source for both the alternating current and direct current circuits may be provided by a standard alternating current 120 volt wall connection, or separate alternating current and direct current sources may be used for each circuit. In particular, with power supplied from a single alternating current the device further includes a variable transformer connected at the primary side to the supply and at the secondary side to the respective circuit and furthermore, includes in the direct current circuit a diode connected in series with the inductor or filter.

The time delay relays, moreover, of each circuit are each individually adjustable in the duration and the period of the current through the respective relay and, therefore, the magnetic particle inspection apparatus of this invention provides simultaneous induction, sequential induction or a combination of simultaneous and sequential induction of pulsed alternating and direct current magnetic fields, in the test material. Accordingly, the regulation of the individual electric currents produce a regulated induced magnetic field having individually adjustable direct current and alternating current components. In this manner, the direct current associated field may be increased for deep subsurface detection without a corresponding interfering increase in the alternating current induced magnetic field. Furthermore, the pulsed induced sequential, simultaneous or combination thereof magnetic fields provide a dynamic motion to the particles for ease of defect observation and allows them to readily respond to defect leakage fields.

Various features of novelty which characterize the invention are pointed out with particularity in the claims annexed to and forming a part of this specification. For a better understanding of the invention, its operating advantages and specific objects obtained by its use, reference should be had to the accompanying drawing and descriptive matter in which there is illustrated and described a preferred embodiment of the invention.

DETAILED DESCRIPTION OF THE PREFERRED EMBODIMENT OF THE INVENTION

For a more complete appreciation of the invention, attention is invited to the following description of the invention, as shown in the attached drawings.

Figure 1:
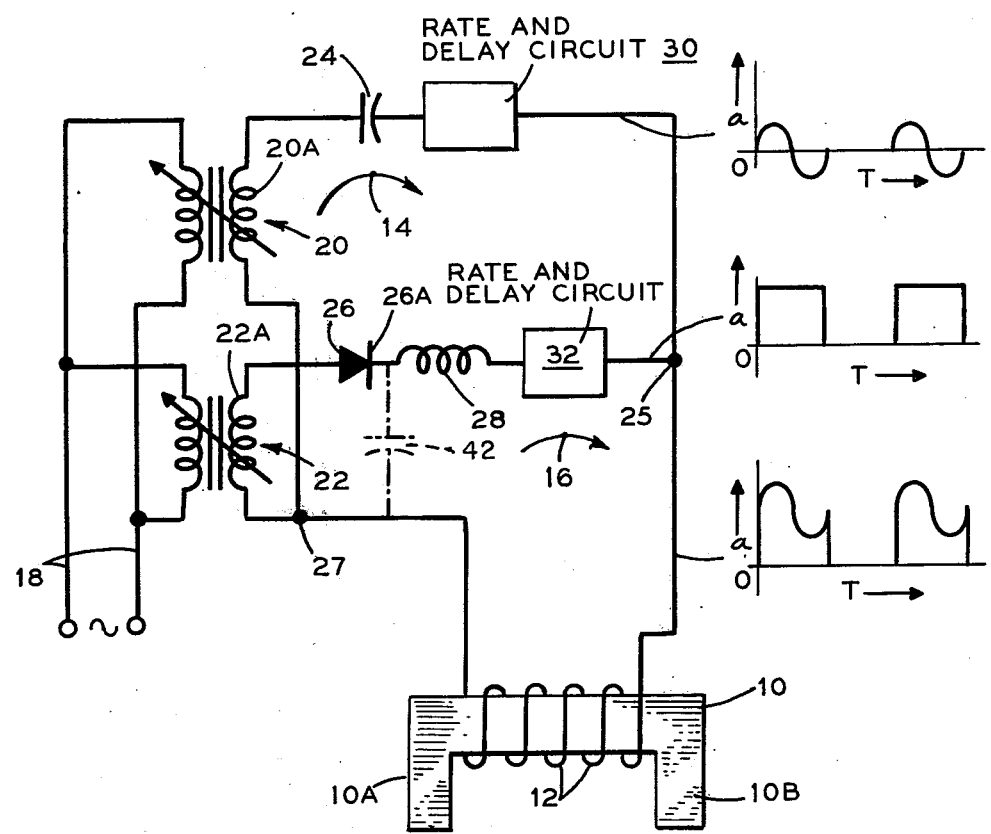
FIG. 1 is a circuit diagram of the preferred embodiment of this invention and, shows schematic illustrations of an illustrative current (a) history of various portions of the circuit.

Referring to FIG. 1, in which is shown the preferred embodiment of the circuit diagram of this invention, a magnetic induction yoke 10 is connected by means of a coil 12 through two parallel circuits, separate portions of which are shown by arrows 14 and 16 respectively, to a power supply (not shown) by means of power supply leads 18. The power supply (not shown) may be any alternating current supply such as ordinary household 120 volt 60 cycle sypply. The circuit 14, or alternating current portion of the circuit, includes a variable transformer 20 having its primary side connected to the leads 18 and a direct current filter 24 serially connected to the secondary side $20_A$. In like manner, the parallel circuit 16 or direct current portion of the circuit also includes a variable transformer 22 having its primary side connected to the leads 18 and comprises an alternating current filter, that is, rectifier or diode 26 connected in series to the secondary side $22_A$ of transformer 22 and a "choke" 28 connected in series to the diode 26. The parallel circuits 14 and 16 alternating and direct current, respectively, are interconnected at 25 to the coil 12 wrapped around the yoke 10 and separate at 27 to complete their respective circuits at transformers 20 and 22, respectively.

Figure 2:
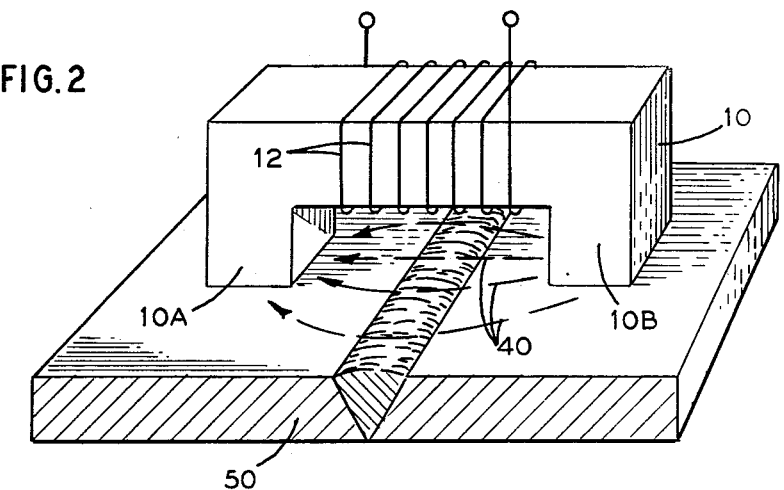
FIG. 2 is a drawing of a typical magnetic yoke in its operating position on a workpiece or test material illustrating the magnetic field lines.
Figure 3A:
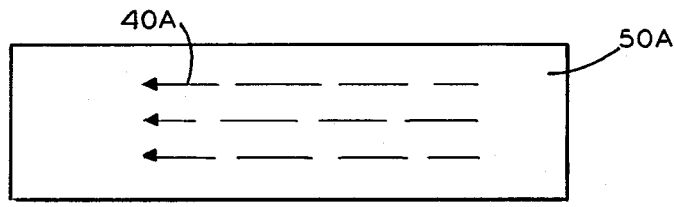
FIGS. 3A, 3B and 3C illustrate three typical workpieces, in section, having direct current induced magnetic fields therein.
Figure 3B:
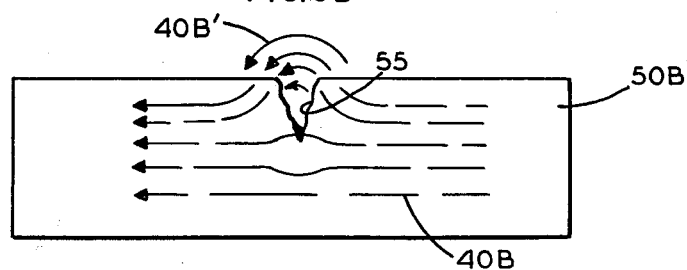
Figure 3C:
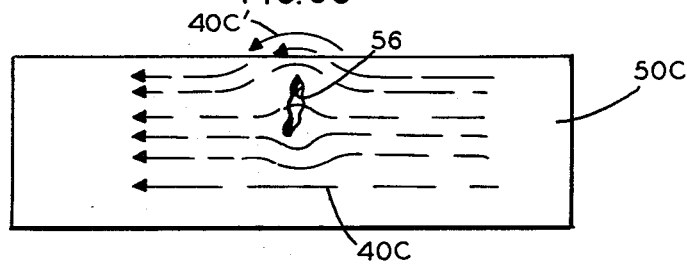

In accordance with magnetic inspection, current flowing through the coil 12 wrapped about the yoke 10 creates a magnetic field within the yoke and induces a magnetic field 40 (FIG. 2) in a desired test material or workpiece 50 (FIG. 2) placed across the ends of the yoke $10_A$ and $10_B$. The magnetic field through the material 50, moreover, completes the circuit of the induced magnetic field in the yoke. Defects in the material, moreover, cause perturbations or distortions of the magnetic field and create magnetic poles on either side thereof which are detectable in a variety of ways. Fig. 3A illustrates a typical workpiece $50_A$ in section having no defects and an induced magnetic field $40_A$ associated therein. Similarly, FIG. 3B illustrates a typical workpiece $50_B$ having a surface defect 55 and indicates the magnetic field perturbation $40_{B'}$ of the induced magnetic field $40_B$. In like manner, FIG. $3_C$ illustrates a typical workpiece $50_C$ having a subsurface defect 56 and indicates the perturbation $40_C$ of the induced magnetic field $40_C$. It is to be noted that the perturbation $40_C$ associated with the subsurface defect 56 may not penetrate the surface of the workpiece $50_C$ if the induced magnetic field $40_C$ is not of sufficient strength or if the defect is substantially below the surface of the workpiece. Accordingly, if the perturbations $40_C$ do not extend through the surface of the workpiece $50_C$ magnetic inspection, for example, by means of magnetic particles dusted onto the surface of the tested workpiece may not indicate the defect. That is, the magnetic particles will not be influenced by the magnetic perturbations $40_C$.

It is well known in the art that the induced magnetic field is related to the current flow. Specifically, referring to FIG. 1 of the invention, the induced magnetic field of yoke 10 results from the algebraic summation of the currents of the two parallel circuits 14 and 16. That is, the induced magnetic field of yoke 10 is the algebraic summation of the magnetic field induced by the alternating current of circuit 14 and the direct current of circuit 16. Hence, in order to be able to independently adjust the strength of the induced magnetic field of each circuit, current adjustment is provided by means of the variable transformers 20 and 22 respectively. Therefore, by proper adjustment of the transformers 20 and 22, the magnetic field induced in the yoke 10 and in a test material connected thereacross due to the direct current circuit 16 alone may be significantly different than the magnetic field induced in the yoke and the test material due to the alternating current circuit 14. Thus, increasing the direct current induced magnetic field for deep subsurface penetration in this device does not also increase the induced alternating current magnetic field which could block the deep subsurface perturbations as explained above in connection with the prior art.

In order to obtain the maximum effects of both the alternating current and direct current induced magnetic fields, the preferred embodiment of the device of this invention further includes a standard electrical adjustable time delay relay 30 and 32 in each circuit 14 and 16, respectively, for example, the commercially available Potter & Brumfield, Type CKB-38-70010. In this manner, a pulsing circuit is produced in which both the pulse rate and the duration of the pulse of both the alternating and direct currents is controlled. For example, a typical alternating current pulse or current history for circuit 14, a direct current pulse or current history for the direct current portion of circuit 16 and the algebraic summation of these pulses as they are applied to the coil 12 are schematically shown in FIG. 1. Hence, the defects in the test material acorss the yoke 10 are exposed to a pulsating direct current magnetic field and sequentially or simultaneously exposed to a pulsating alternating current magnetic field. Moreover, the pulsating magnetic fields of this invention significantly influence the magnetic particle's response to a deep subsurface defect or perturbed magnetic field thereof.

In operation with magnetic particles, for instance, the yoke 10 is placed in contact with the test material and an alternating supply source is connected to the leads 18. Magnetic powder particles placed or dusted upon the test material between the ends $10_A$ and $10_B$ of the yoke are then exposed to the induced pulsating magnetic fields. By proper adjustment of the rate and duration of each current, a small leakage field from a defect deep below the surface of the material is detected by the magnetic particles due to the high mobility created therein by the pulsating alternating current portion of the induced magnetic field. Furthermore, since the direct current magnetic field holds the magnetic particles stationary and the alternating current magnetic field induces a mobility to the particles, the pulsating direct current and alternating current magnetic fields influences the particles such that they, in effect, "walk" along the test material in a pulsed dynamic manner. For example, a direct current perturbed magnetic field due to a defect holds the particles and a subsequent or simultaneous alternating current magnetic field mobilizes the remaining particles. Thereafter, if the direct current pulse ceases the alternating current field if still "on " mobilizes all the particles. Subsequently, a second direct current pulse or a residual direct current magnetic field will perturb the field at the defect which will hold the magnetic particles influenced thereby. In effect, a dynamic or moving picture of the defect is created and is readily recognized thereby. Accordingly, the "walk-ing" of the magnetic particles across the surface of the test material is produced by the combined alternating current and direct current induced pulsed magnetic fields whether simultaneously or sequentially applied. That is, even when the alternating current is only applied during the "off" time of the direct current, sequentially, or only during the "on " time of the direct current, simultaneously, "walking" of the particles is produced by the direct and residual direct current induced magnetic fields and the skin effect of the surface alternating magnetic field.

The magnetic inspection method and device or apparatus of this invention was tested on two test plates having carefully measured defects "holes" therein (see Table 1) versus a like yoke influenced by (1) alternating current alone and (2) direct current alone. Using only the alternating current or direct current magnetizing setup, holes Nos. 7 and 8 were detected in test plate #1 and hole No. 3 in test plate #2 was the deepest defect detectable. Whereas, the device of this invention detected holes Nos. 7 and 8 and the deeper holes Nos. 5 and 6 of test plate #1; and also, detected holes numbered 1 through 5 of test plate #2. Accordingly, the device and method of this invention provided a 60% increase in deep defect detection; and, also provided a dynamic visual defect indication, "walking" of the particles, not provided by other methods.

TABLE 1.

| Hole No. | Hole Diameters | PLATE 1 Hole Length (L) | Below Surface Hole Depth |
|---|---|---|---|
| 1 | .0312" (.794 mm)* | .000" (Drill Broke) | — |
| 2 | .0312" (.794 mm) | 1.098" (27.9 mm) | .052" (1.32 mm) |
| 3 | .0312" (.794 mm) | .118" (Drill Broke) | .046" (1.17 mm) |
| 4 | .0312" (.794 mm) | 1.012" (25.7 mm) | .038" (0.97 mm) |
| 5 | .0312" (.794 mm) | .395" (10.2 mm) | .035" (0.89 mm) |
| 6 | .0312" (.794 mm) | .992" (25.2 mm) | 0.24" (0.61 mm) |
| 7 | .0312" (.794 mm) | .985" (25.0 mm) | .021" (0.53 mm) |
| 8 | .0312" (.794 mm) | 1.067" (27.1 mm) | .012" (0.31 mm) |

| Hole No. | Hole Diameters | PLATE 2 Hole Length (L) | Below Surface Hole Depth |
|---|---|---|---|
| 1 | .0625" (1.587 mm) | 1.010" (25.6 mm) | .010" (0.25 mm) |
| 2 | .0625" (1.587 mm) | 1.013" (25.7 mm) | .025" (0.63 mm) |
| 3 | .0625" (1.587 mm) | 1.006" (25.4 mm) | .040" (1.02 mm) |
| 4 | .0625" (1.587 mm) | .981" (25.0 mm) | .054" (1.37 mm) |
| 5 | .0625" (1.587 mm) | 1.003" (25.4 mm) | .072" (1.83 mm) |
| 6 | .0625" (1.587 mm) | .990" (25.2 mm) | .086" (2.18 mm) |
| 7 | .0625" (1.587 mm) | .984" (25.0 mm) | .101" (2.57 mm) |
| 8 | .0625" (1.587 mm) | .988" (25.1 mm) | .147" (3.74 mm) |

*Where (") indicates inches and (mm) indicates milimeters.

Further, in the preferred embodiment of this invention it is found that the reactance (X) of the choke, inductor 28, should be greater than 10 times the impedance (Z) of the yoke, i.e.

$$X_L > 10\ Z_{yoke}$$

and that the reactance of the filter or capacitor 24 should be less than one tenth of the impedance of the yoke, i.e.

$$X_C < Z\ yoke/10$$

In passing it should be noted that the impedance (Z) is a measure of the total opposition to current flow in an alternating current circuit, usually represented in complex notation as $Z = R + iX$, where $R$ is ohmic resistance and $X$ is the opposition caused by inductance or capacitance in an alternating current circuit.

In addition, another embodiment of the invention includes a capacitor 42 (shown in phantom in FIG. 1) connected at one end between the cathode 26A and the choke 28 and at the other end to the terminal portion of coil 12, to ensure direct current flow in the circuit 16 for all phase combinations of the transformers 20 and 22.

Furthermore, it is apparent to one skilled in the art that a direct current source could be provided to replace the alternating current source (not shown), transformer 22 and rectifier 26 of circuit 16, however, the preferred embodiment discussed and shown herein not only provides an improved magnetic particle inspection method, but also has the further advantage of relative compactness and simplicity offered by a single power source.

In accordance with this invention, a method and a device for improved nondestructive magnetic particle inspection is provided.

The embodiments of the invention in which an exclusive property or privilege is claimed are defined as follows:

1. A method for detecting flaws in a magnetizable workpiece, comprising the steps of:
   depositing magnetic particles on the workpiece,
   subjecting the workpiece to pulsed alternating and direct current magnetic fields, and
   adjusting the rate and duration of pulsing of the alternating and direct current magnetic fields to improve the detection of flaws in the workpiece.

2. The method according to claim 1 including the step wherein the pulsed alternating and direct current magnetic fields are simultaneously applied to the workpiece.

3. The method according to claim 1 including the step wherein the pulsed alternating and direct current magnetic fields are sequentially applied to the workpiece.

4. An apparatus for detecting flaws in a magnetizable workpiece having magnetic particles deposited thereon, the apparatus comprising a magnetizable yoke disposed on the workpiece, a magnetizing coil wound about the yoke, an alternating current circuit for delivering alternating current to the magnetizing coil, a direct current circuit including a rectifier for converting alternating current to direct current and delivering direct current to the magnetizing coil, the alternating and direct current circuits being connected in parallel to a common source of alternating current, each circuit including an adjustable output transformer for regulating current input to the magnetizing coil, the alternating and direct current circuits including filters to prevent passage therethrough of direct and alternating currents, respectively, and adjustable time delay relays for producing pulsed alternating and direct currents, respectively, and for regulating the duration and rate of pulsing of the alternating and direct currents being delivered to the magnetizing coil.

5. The apparatus according to claim 4 wherein the direct current circuit includes a capacitor having one end connected between the filter and the rectifier and the other end connected between the transformer and the magnetizing coil to insure direct current flow through the circuit for all phase combinations of said transformers.

* * * * *

UNITED STATES PATENT AND TRADEMARK OFFICE
CERTIFICATE OF CORRECTION

PATENT NO. : 4,058,762
DATED : November 15, 1977
INVENTOR(S) : Amos Earl Holt et al It is certified that error appears in the above-identified patent and that said Letters Patent are hereby corrected as shown below:

Column 1, line 38, the second word "of" after the word penetration and before the word fusion should read --or--.

Column 3, line 11, "scross" should read --across--.

Column 5, line 32, "acorss" should read --across--.

Column 6, line 37-38, TABLE 1 fourth column "0.24" should read --.024--.

Signed and Sealed this

Twenty-second Day of January 1980

[SEAL]

Attest:

SIDNEY A. DIAMOND

Attesting Officer

Commissioner of Patents and Trademarks